United States Patent [19]

Manian

[11] Patent Number: 4,930,893
[45] Date of Patent: Jun. 5, 1990

[54] ELECTROPHORESIS IMAGING SYSTEM

[75] Inventor: Bala S. Manian, Saratoga, Calif.

[73] Assignee: Molecular Dynamics, Sunnyvale, Calif.

[21] Appl. No.: 173,434

[22] Filed: Mar. 25, 1988

[51] Int. Cl.$^5$ .................. G01N 21/41; G01B 9/02
[52] U.S. Cl. ........................ 356/344; 356/128/353
[58] Field of Search ............. 356/128, 129, 353, 361, 356/362, 344

[56] References Cited

U.S. PATENT DOCUMENTS

| | | | |
|---|---|---|---|
| 3,617,130 | 11/1971 | Kelly et al. | 356/355 |
| 4,225,240 | 9/1980 | Balasubramanian | 356/360 |
| 4,441,811 | 4/1984 | Melezoglu et al. | 356/128 |
| 4,547,071 | 10/1985 | Teitelbaum | 356/344 |

FOREIGN PATENT DOCUMENTS

| | | |
|---|---|---|
| 113672 | 7/1984 | European Pat. Off. |
| 113673 | 7/1984 | European Pat. Off. |
| 113674 | 7/1984 | European Pat. Off. |
| 113677 | 7/1984 | European Pat. Off. |
| 115777 | 8/1984 | European Pat. Off. |
| 160948 | 11/1985 | European Pat. Off. |

OTHER PUBLICATIONS

Hariharan, P. "Simple Laser Interferometer with Variable Shear and Tilt", *Applied Optics*, vol. 14, No. 5 (May 1975), pp. 1056–1057.

Toshio Takagi et al., "Real-Time Monitoring of Polyacrylamide Gel Electrophoresis by Schlieren Optics," *Journal of Biochemistry*, vol. 102, No. 4, 1987, pp. 681–684.

Advertisement for *ATTO Schlierograph*, model ED-S-100, n.d.

Erik Fries, "Visualization of Protein Zones in Preparative Electrophoresis and Carrier Ampholyte Zones on Isoelectric Focusing in Gel Slabs by Two Light Refraction Metohds," *Analytical Biochemistry*, vol. 70, 1976, pp. 124–135.

R. C. Allen et al., "A vertical Flat-Bed Discontinuous Electrophoresis System in Polyarcylamide Gel," *Analytical Biochemistry*, vol. 16, 1966, pp. 457–465.

Eugene Hecht et al., *Optics*, Publ. 1974 by Addison-Wesley Publishing Company (Reading, Mass.) see pp. 474–478.

Robert A. Sprague et al., "Quantitive Visualization of Large Variation Phase Objects", *Applied Optics*, vol. 11 No. 7, Jul. 1972, pp. 1469–1479.

Nicholas Catsimpoolas, "Transient State Isoelectric Focusing in Polyacrylamide Gel (Scanning Isoelectric Focusing)," 15 pages.

George Olson et al., "Computer-Controlled Electrophoresis Microscope," *SPIE*, vol. 232, 1980 *Internaltional Optical Computing Conference*, 1980, pp. 54–61.

Arthur Elliot, "The Instantaneous Monitoring of Polyacrylamide Gels during Electrophoresis," *The Biochemical Journal*, vol. 159, No. 3, 1976, pp. 743–748.

Primary Examiner—Richard A. Rosenberger
Attorney, Agent, or Firm—Thomas Schneck

[57] ABSTRACT

A method and system for imaging unstained smaple material constituents on a gel electrophoresis unit. The system includes a gel electrophoresis unit, preferably having a pH gradient gel thereon, phase detection optics including a collimated light source, shearing interferometer, phase contrast microscope or schlieren microscope, an image digitizer, and data processing electronics, such as a computer, for determining the concentration of sample constituents at each position on the electrophoresis unit. The method relies on the difference in index of refraction between sample material and gel material to introduce optical path differences in light rays passing through the material. The modified light is subjected to shearing interferometry to locate gel-sample boundaries, phase imaging to directly image the sample, or a laser scanner for directly measuring the deviation in a light beam due to the sample.

6 Claims, 4 Drawing Sheets

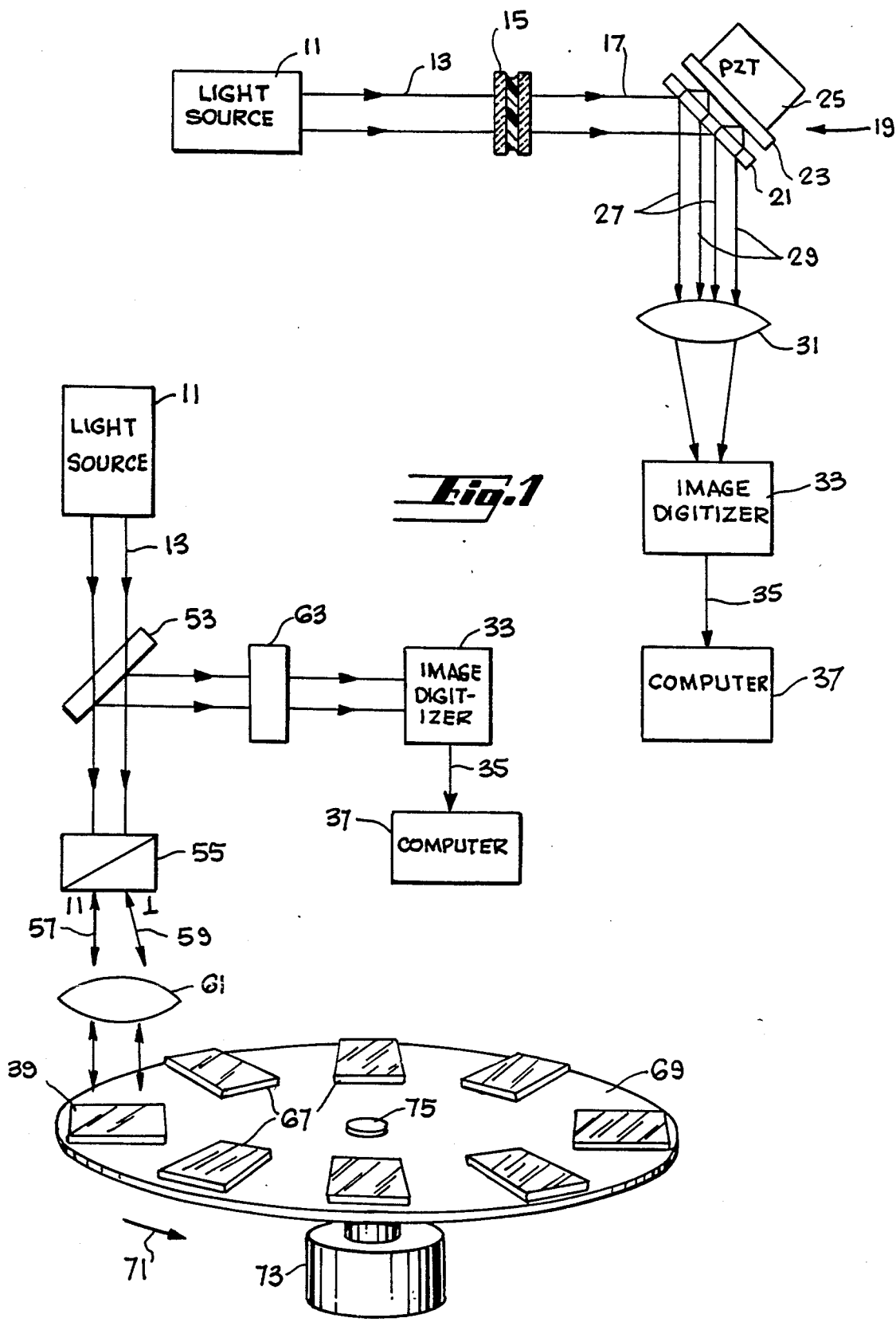

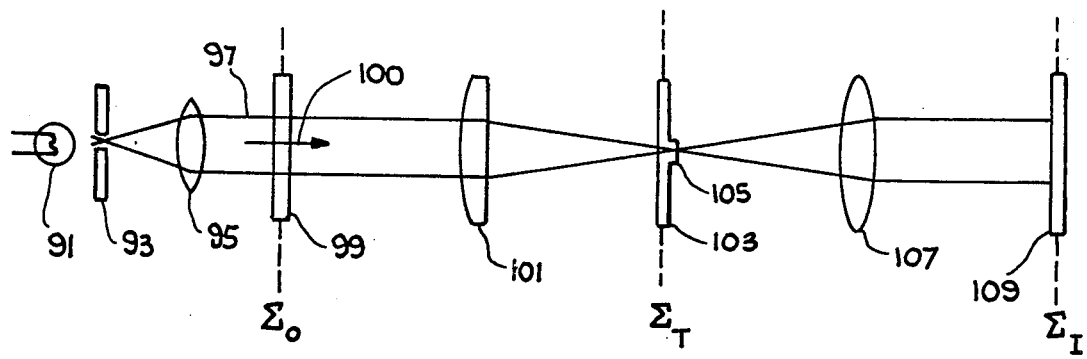
_Fig. 6_
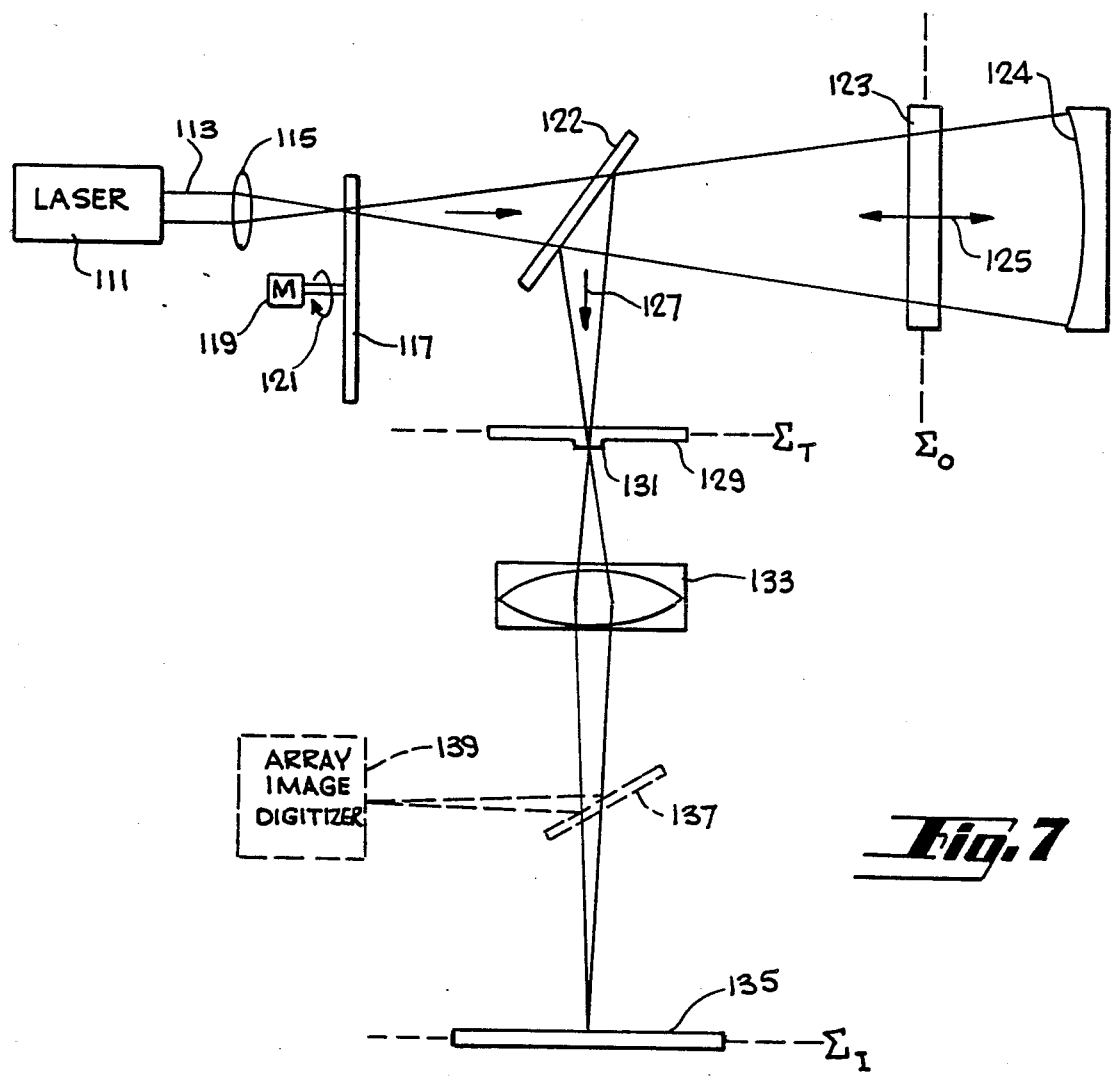
_Fig. 7_

ELECTROPHORESIS IMAGING SYSTEM

DESCRIPTION

1. Technical Field

The present invention relates to optical systems and measuring methods for the imaging and detection of sample constituents in gel electrophoresis.

2. Background Art

Electrophoresis, as used in the fields of biology, molecular biology, biochemistry, clinical chemistry and medicine, is an analytical technique for separating and detecting biologically important molecules in a sample. Important applications include the determination of a sample's homogeneity, the determination of molecular weights of proteins and nucleic acids, the mapping of nucleic acid primary structures, i.e. DNA and RNA sequence analyses, and the definition of phenotypic variants of a protein at the molecular level. A variety of techniques have been developed in order to accomplish these tasks. However all of the techniques rely on the fact that every molecular species has a unique combination of size, shape, charge, density and subunit structure. Each of the electrophoretic techniques uses one or more of these parameters to cause varying degrees of molecular separation via the migration of the molecular species under the influence of an electric field. One widely used set of techniques, called "gel electrophoresis" involves the movement of sample constituents of various molecular species through a polymer matrix or gel.

Analysis of the electrophoresis run depends on visualization of the protein or nucleic acid samples on the gel matrix. These samples are usually transparent. In order to visualize these components, they are usually processed with one of a variety of stain/destain cycles and then photographs of the image taken for analysis and publication. These staining processes develop colored bands whose optical densities are assumed to be approximately proportional to the amount of peptide linkages present and therefore to the total amount of protein in a band. Staining does introduce a number of uncertainties including the stoichiometry of stain to complex. The attachment of a stain to a protein changes the nature of the protein, potentially affecting the mobility characteristics in an electric field. As a result, staining cannot be performed until the completion of electrophoresis, making visual monitoring of the electrophoresis process impossible. Further, after staining other analyses of a particular component on the plate are usually not performed, since staining may have altered other intrinsic characteristics of the protein. Presently available electrophoresis staining techniques are also time consuming, reducing their usefulness in clinical and medical applications.

It is an object of the present invention to produce a quantitative electrophoresis imaging method which does not require staining or radiolabeling.

DISCLOSURE OF THE INVENTION

The above object has been met with an optical system and measuring method which uses phase modulation instead of staining to image sample material constituents in a gel. The method relies on the fact that although electrophoresis gel materials and sample materials are both transparent, and thus without staining are invisible to the human eye for visual analysis, they have different indices of refraction, and thus can be distinguished by means of the contrasting refractive indices and differing optical path lengths through gel and sample.

At any point in time, the indices of refraction at a particular location and at another location proximate thereto may be measured and compared, the difference between the measured indices indicating the presence of a gel-sample boundary between those locations. Accordingly, in one embodiment of the present invention, a gel electrophoresis unit containing sample material thereon is illuminated with a collimated light beam, the difference in refractive indices between gel material and sample material creating optical path differences that modify the wavefront of light passing through or reflected off the back of the electrophoresis unit. The modified light beam is then passed through a shearing interferometer to produce an interferogram representing the spatial rate of refractive index change at every point of the electrophoresis unit. The interferogram is scanned with an image digitizer to produce a data signal. The signal is integrated to obtain the pattern of phase values of the modified wavefront, the phase values being proportional to the sample concentration at each point of the electrophoresis unit. These phase values for each point at any given instant of time may be stored in a computer memory for further analysis or displayed in an eye readable form.

In another embodiment, an electrophoresis unit is illuminated with a collimated light beam, the refractive index differences between gel and sample material creating optical path differences that modify the wavefront of the light beam. The modified light beam can be expressed as a superposition of the direct unmodified light beam and a diffracted component. The direct or zero order component is then phase shifted by 90° by a phase plate in a transform plane or selectively absorbed by a knife edge, or both phase shifted and partially absorbed. The image formed in an image plane is an amplitude modulated representation of the optical path differences caused by the sample constituents in the gel electrophoresis unit. Phase shifting with or without some absorption of the direct light produces an image which is a direct correspondence with the index of refraction distribution in the electrophoresis unit, while absorption only of the direct light produces an image which corresponds to the rate of change or slope of the refractive index distribution.

Another embodiment uses a laser scanner to directly measure the angular deviation of a laser beam as it passes through an electrophoresis unit, the deviation appearing as a beam displacement at a position detector.

BRIEF DESCRIPTION OF THE DRAWINGS

FIG. 1 is a schematic view of a first embodiment of a system of the present invention for carrying out a method of the present invention.

FIG. 2 is a schematic view of a second embodiment of a system of the present invention.

FIG. 6 is a schematic view of a third embodiment of a system of the present invention.

FIG. 7 is a schematic view of a fourth embodiment of a system of the present invention.

BEST MODE FOR CARRYING OUT THE INVENTION

Figure 3:
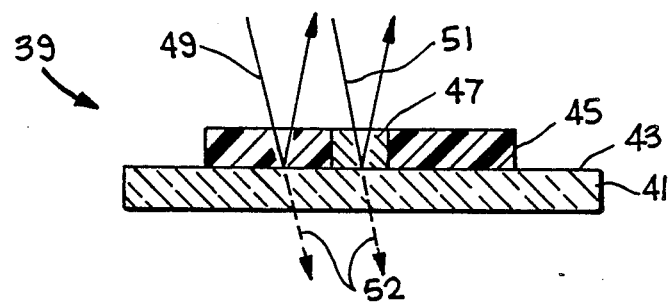
FIG. 3 is side section of a gel electrophoresis unit for use with the system of FIGS. 1 and 2.

With reference to FIG. 1, an electrophoresis imaging system of the present invention carrying out a method of the present invention comprises a collimated light source 11 emitting a collimated light beam 13 that illuminates an electrophoresis unit 15. Light beam 13 may, for example, be a laser beam emitted by a laser 11. Beam 13 typically has a diameter or spot size of about 25 mm for an electrophoresis unit of similar size, but may also be enlarged further in order to completely illuminate large electrophoresis units. Alternatively, in the case of standard size units 50 mm or 100 mm square, beam 13 may scan electrophoresis unit 15. Electrophoresis unit 15 may be any plate or cartridge used for electrophoresis. Small prepared disposable cartridges on the order of 25 mm in size are preferred over the larger 100 mm size standard plates because the preprepared cartridges eliminate gel preparation steps, allowing less experienced persons to use them, require less sample material and achieve more reproducible results. Such small formats in combination with the high resolution of the present system can reduce electrophoresis run times to about an hour or even less. Typically, the electrophoresis unit 15 is a gel electrophoresis unit containing precast gel material, such as a pH gradient gel, and also having a small amount of sample material inserted at one end on the gel and allowed or caused to migrate. For example, the gel may be an acrylamide polymer matrix. Alternatively, other types of electrophoresis units may be used, provided the medium in which the sample moves has a different index of refraction than sample material to enable imaging and detecting of sample constituents without staining.

The different indices of refraction create optical path differences for light beam 13 passing through material on electrophoresis unit 15. The light beam 13 is thereby modified, i.e. the optical path differences cause a change in phase of portions of the wavefronts of the light beam relative to other portions depending on the particular local concentration of sample material which that portion passes through. The modified light beam 17 then passes through a shearing interferometer 19 in the path of the light beam in order to make visible the phase changes of the wavefronts. The shearing interferometer 19 in FIG. 1 comprises a pair of closely spaced plates 21 and 23 oriented in the beam path at an approximately 45 degree angle. Typically, plates 21 and 23 are substantially parallel, although this is not absolutely essential in one dimensional electrophoresis provided that the plates be parallel at least in the direction orthogonal to sample movement. If the plates are not exactly parallel, a straight line interference pattern results with the presence of sample constituents introducing additional dark lines at the sample gel-boundaries. First plate 21 is fixed, while second plate 23 is moved by means of a piezoelectric transducer or PZT 25 attached to the back of second plate 23, so as to alter the spacing between the plates.

Modified light beam 17 strikes first plate 21 and a portion 27 of the light is reflected. The remainder of the light is transmitted through first plate 21, across the variable space between plates 21 and 23, is reflected from second plate 23 back across the variable space between plates and through first plate 21. The portion 29 of light reflected from second plate 23 superposes with the portion 27 of light reflected from first plate 21 to form an interferogram. A lens 31 in the path of light 27 and 29 reflected from interferometer 19 images the interferogram onto an image digitizer 33. Image digitizer 33, which is typically a CCD array camera, produces an electrical data signal 35 proportional to the intensity of light at each point of the interferogram. The data signal 35 is received by a computer 37 in electrical communication with image digitizer 33. The computer 37 analyzes the data signal 35, as for example by integrating over position the intensity of light received by digitizer 33 so as to reproduce the concentration of sample at each point on electrophoresis unit 15.

One way in which data signal 35 can be analyzed is by the method disclosed in U.S. Pat. No. 4,225,240 issued to the present inventor Briefly, the intensity I(x) of the interferogram, where x corresponds to a position on an electrophoresis unit, is the superposition of the intensities $I_0(x)$ and $I_1(x)$ of light portions 27 and 29 respectively taking into account the optical path difference $\Delta(x)$ of light of the two portions 27 and 29.

$$I(x) = I_0(x) + I_1(x) \cos\left(\frac{2\pi}{\lambda} \Delta(x)\right),$$

where $\lambda$ is the wavelength of light beam 13. Moving the second plate 23 by means of piezoelectric transducer 25 so that the optical path length of light portion 29 varies in steps, we obtain three interferograms represented by the equations:

$$I(x) = I_0(x) + I_1(x) \cos\left(\frac{2\pi}{\lambda} \Delta_0(x)\right) \quad (1)$$

for a first plate separation $Z_0$ $$I(x) = I_0(x) - I_1(x) \sin\left(\frac{2\pi}{\lambda} \Delta_0(x)\right) \quad (2)$$

for a second plate separation $Z_0 + \lambda/4$, and $$I(x) = I_0(x) - I_1(x) \cos\left(\frac{2\pi}{\lambda} \Delta_0(x)\right) \quad (3)$$

for a third plate separation $Z_0 + \lambda/2$, where $\Delta_0(x)$ is the optical path difference of light passing through electrophoresis unit 15 as a function of position x. With three equations (1), (2) and (3) and three unknowns $I_0(x)$, $I_1(x)$ and $\Delta_0(x)$ we can solve for $\Delta_0(x)$. As discussed further below, integrating $\Delta_0(x)$ over position we get the amount of the phase shift of light passing through electrophoresis unit 15 which is proportional to the concentration of sample material at each position. Although we have described this method in terms of one dimensional electrophoresis, it is easily extended to two dimensions.

With reference to FIG. 2, another embodiment of an electrophoresis system of the present invention is shown. Again, a collimated light source 11, such as a laser, emits a collimated light beam beam 13 directed toward an electrophoresis unit 39. Again the light passing through gel and sample material on electrophoresis unit 39 is modified and the modified light is passed through a shearing interferometer, here a Nomarski microscope, to produce an interferogram. The interferogram is imaged onto an image digitizer 33 which produces an electrical data signal for analysis by a computer 35. Alternatively, the interferogram may be viewed directly by forming an image on a rear projection screen or in a camera positioned in the same location as or at a conjugation point of image digitizer 33.

As seen in FIG. 3, an electrophoresis unit 39 may comprise at least one cartridge or support plate 41 on which is disposed a gel material 45, and onto which is inserted a sample material 47. Support plate 41 may have a reflective coating 43 behind gel material 45 so that light illuminating electrophoresis unit 39 and passing through material 45 and 47 on plate 41 is reflected back through the material 45 and 47. Alternatively, support plate 41 may be transparent and may lack reflective coating 43 so as to produce a light transmissive electrophoresis unit 39, represented by phantom light rays 52. In either case, since sample material 47 has a different refractive index, typically about 1.35, than gel material 45, typically about 1.50, light rays 49 passing through gel material travel over a longer optical path length than light rays 51 passing through sample material.

Electrophoresis unit 15 is typically reflective when used in the system in FIG. 2 and typically transmissive when used in the system in FIG. 1. Alternatively, however it is readily apparent that the system in FIG. 1 can be modified to accept reflective electrophoresis units, such as by including a beamsplitter similar to beamsplitter 53 in FIG. 2 between light source 11 and electrophoresis unit 15 and placing interferometer 19, lens 31 and image digitizer 33 in the path of light reflected from electrophoresis unit 15 and the beamsplitter. Likewise, the system in FIG. 2 can be modified to accept transmissive electrophoresis units by removing beamsplitter 53, adding an additional lens and prism, similar to lens 61 and prism 55, on the opposite side of electrophoresis unit 39 from light source 11, and moving polarizer 63 and image digitizer 33 into the path of light transmitted through electrophoresis 15 and the additional lens and prism.

Referring again to FIG. 2, the shearing interferometer comprising elements 53, 55, 61 and 63 is a Nomarski microscope which operates in the manner described in the two-part article by Delbert Lessor, John Hartman and Richard Gordon entitled "Quantitative Surface Topography Determination by Nomarski: Reflective Microscopy" and appearing in the *Journal of the Optical Society of America*, Vol. 69, No. 2, February 1979, pp. 357–365 and *Applied Optics*, vol. 19, No. 17, Sept. 1, 1980, pp. 2998–3009. Briefly, a Wollaston prism 55 is fabricated from two wedge pieces of birefringent material with their respective first optical axes orthogonal to each other. The prism separates collimated light beam 13 into two beams 57 and 59 polarized respectively parallel to and perpendicular to the plane of the electrophoresis unit 39 and offset in a shear direction of the prism. An objective lens 61 is mounted so that its rear focal plane coincides with the plane from which the two beams appear to split. On reflection, the prism recombines the light of each polarization so they are again collinear. A polarizer 63 oriented to pass light with a linear polarization oriented approximately 45° with respect to both polarization components of beams 57 and 59 allows the two beams to add vectorially, the ray producing the interferogram received by image digitizer 33, a rear projection screen or a camera.

Also shown in FIG. 2, the system is capable of sequentially imaging, if desired, a plurality of electrophoresis units 67 supported on a table 69. For example, table 69 may rotate in a direction indicated by arrow 71 so that each electrophoresis unit 67 may be observed in turn. A stepper motor 73 connected to table 69 via a spindle 75 may be used to turn table 69. Other multiple electrophoresis unit configurations are also possible.

Figure 4:
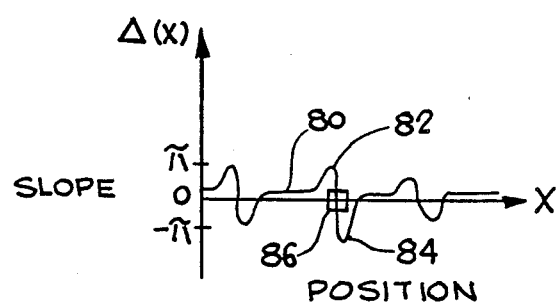
FIG. 4 is a graph of phase difference versus position representing an interferogram produced by the systems of FIGS. 1 and 2.
Figure 5:
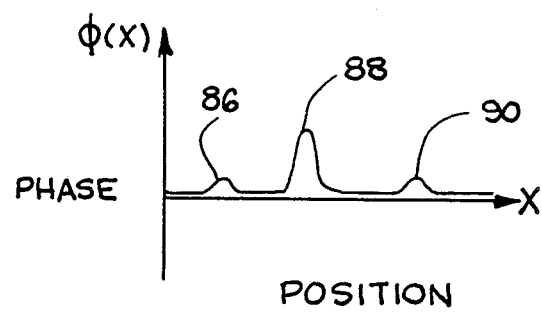
FIG. 5 is a graph of sample material concentration versus position obtained by integrating over space the interferogram data represented by the graph in FIG. 4.

With reference to FIGS. 4 and 5, the interferogram received by image digitizer 33 in the systems of FIGS. 1 and 2, and converted to data signals are analyzed as described above to obtain the optical path difference or slope $\Delta_0(x)$. This represents the spatial rate of change of index of refraction of material on the electrophoresis plate. $\Delta_0(x)$ is approximately zero at 80 in FIG. 4 corresponding to regions on the electrophoresis plate containing only gel material, i.e. no sample material, and at 86 corresponding to regions where sample material bands are heated, i.e. between the gel-sample boundaries. A change of refraction index occurs at a gel-sample boundary 82 which appears as a non-zero optical path difference $\Delta_0(x)$. Since each occurrence of a sample constituent is represented by two boundaries, one from gel to sample and one from sample to gel, the presence of sample material at a given location appears as two non-zero optical path difference measurements 82 and 84, one positive and one negative. Integrating the optical path difference or slope $\Delta_0(x)$ over position, we obtain the phase $\phi(x)$ of the modified light beam after having passed through material on the electrophoresis unit. The phase $\phi(x)$ is proportional to the concentration of sample material at position x relative to gel material. In FIG. 5, the presence of sample material is indicated at positions 86, 88 and 90 with local phase maxima.

With reference to FIG. 6, a light source 91 shines light through a stop 93 with a pinhole aperture and through a collimating lens 95 to produce a collimated light beam 97. Collimated beam 97 passes once through a gel electrophoresis unit 99 with sample material thereon lying in an object plane $\Sigma_o$, as indicated by arrow 100. The substantially planar wavefront of collimated beam 97 becomes phase modulated, since the optical path length through the electrophoresis unit 99 varies from point to point as the refractive index varies with the concentration of sample material. The embodiment in FIG. 6, which is a Zernike phase contrast microscope, provides a means for viewing the degree of phase modulation by converting it into an amplitude modulated image.

A transform lens or objective 101 brings the direct or zeroth-order component of the modulated wavefront to a focus in a transform plane $\Sigma_T$, essentially forming a small image of the aperture of stop 93. A phase plate 103 lies in the transform plane $\Sigma_T$ and has a small raised disk 105 at its center. The zeroth-order component of the wavefront passes through disk 105 and is retarded with respect to the diffracted component by 90°. The diffracted component of the wavefront, containing information about sample constituents in electrophoresis unit 99 passes through phase plate 103 substantially outside of disk 105 and is thereby unaffected. Alternatively, phase plate 103 may have a central indentation, instead of a disk, capable of producing a 90° phase advance of the zeroth-order component relative to the diffracted component. Either indentation or disk 105 may also have a thin film for absorbing a portion of the zeroth-order direct light.

After passing through the phase plate 103, an imaging lens 107 produces an amplitude modulated image of the sample constituents in an image plane $\Sigma_I$, where a photographic plate 109, densitometer or other viewing means is located. If phase plate 103 has a raised central disk 105, sample constituents in the gel will appear bright against a dark background, while the opposite would be the case for a central indentation in phase plate 103.

Another embodiment of a phase contrast microscope operating in a reflective rather than a transmissive mode is seen in FIG. 7. A laser 111 produces a beam 113 which is focused by a focusing lens 115 onto a rotating diffuser 117. Rotating diffuser is turned by a motor 119 lying away from the optical axis, as indicated by arrow 121, and functions to destroy the coherence of beam 113. The beam passing through beamsplitter 122 passes once through gel electrophoresis unit 123, is reflected by spherical mirror 124 and passes again through gel electrophoresis unit 125, indicated by arrows 125. Unit 125 and spherical mirror 124 are far enough away from rotating diffuser 117 so that the wavefront of the light, though spherical, appears substantially planar.

The modulated light is reflected by beamsplitter 122, as indicated by arrow 127, and the zeroth-order component thereof is brought to a focus in a transform plane $\Sigma_T$, essentially forming an image of the light source on diffuser 117 as diffracted by sample constituents in electrophoresis unit 123 in object plane $\Sigma_o$. Again, a phase plate 129 in transform plane $\Sigma_T$ with a central raised disk or indentation retards or advances the phase of the zeroth-order component of the modulated light relative to the diffracted component. An imaging lens 133 then forms an amplitude modulated image in image plane $\Sigma_I$, where a view means such as a photographic plate is located. Alternatively, several different viewing means may be provided, as for example an array image digitizer 139 receiving the image via beamsplitter 137.

Figure 8:
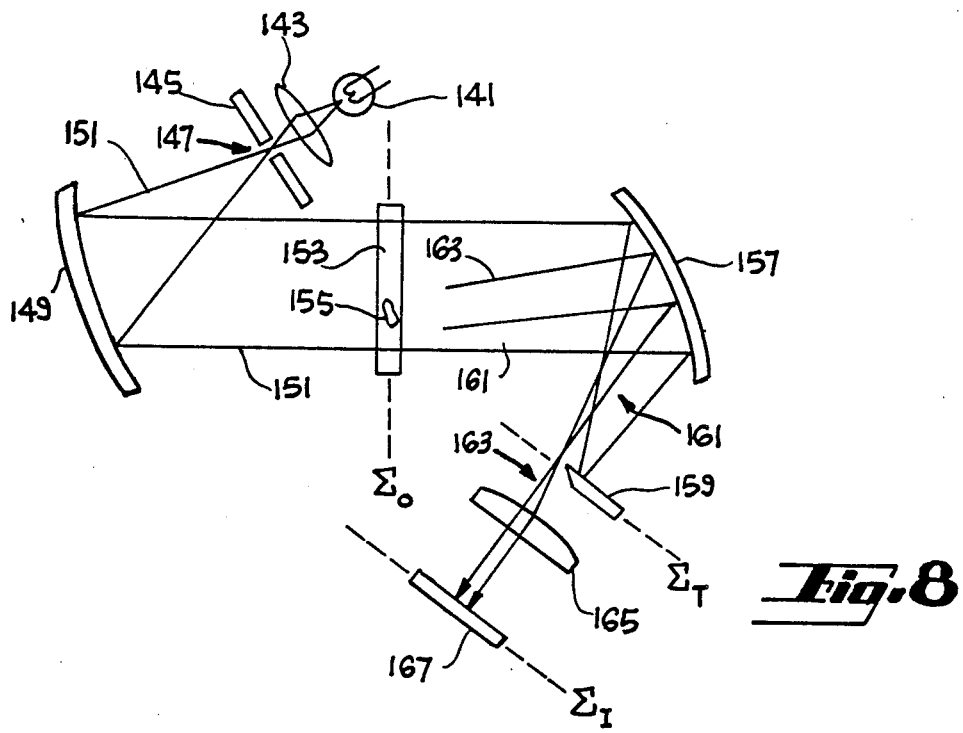
FIG. 8 is a schematic view of a fifth embodiment of a system of the present invention.

With reference to FIG. 8, another method of producing a discernible image of phase objects is the dark ground or schlieren method. A light source 141 emits light which is brought to a focus by a condenser lens 143 onto a stop 145 with an aperture 147 therein. The light 151 is then reflected and collimated by a spherical mirror 149 so as to illuminate a gel electrophoresis unit 153 having sample constituents 155 therein. Again light 151 modulated by constituents 155 in electrophoresis unit 153 is composed of an undiffracted or zeroth-order component 161 and a diffracted component 163. The modulated light is reflected and focused by a spherical mirror 157, the zeroth-order component 161 being brought to a focus in a transform plane $\Sigma_T$. A knife edge, or other absorbing obstruction lies in transform plane $\Sigma_T$ and is movable so as to completely or partially block zeroth order component 161, while letting a substantial portion of diffracted light 163. Diffracted light 163 is then imaged by an imaging lens 165 onto an image plane $\Sigma_I$ where a viewing means 167, such as a photographic plate, image digitizer or the like, is located. Lens may take the place of spherical mirrors 149 and 157, although mirrors are preferred for a compact light path.

The image formed by the schlieren set up in FIG. 8 is a measure of the slope of the index of refraction distribution in electrophoresis unit 153, whereas the image in the phase contrast microscope set up in FIGS. 6 and 7 is a direct measure of the index of refraction distribution.

Figure 9:
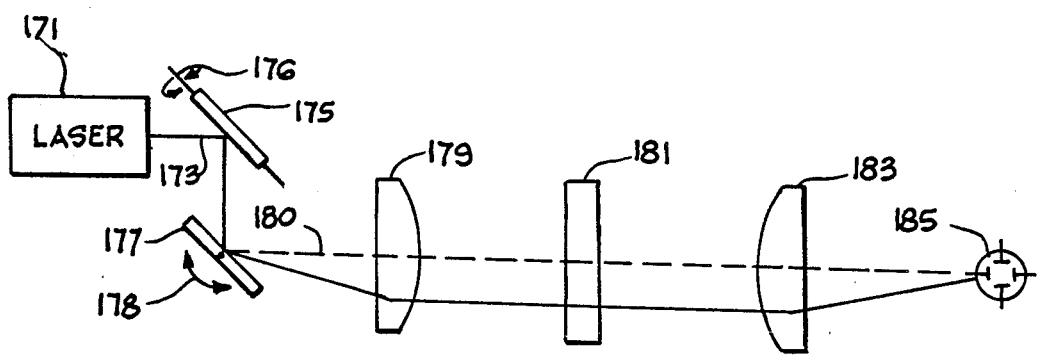
FIG. 9 is a schematic view of a sixth embodiment of a system of the present invention.

With reference to FIG. 9, rather than using interferometry, as in the embodiments of FIGS. 1 and 2, or phase imaging, as in the embodiments in FIGS. 6-8, the index of refraction, or optical path length can be measured directly using a laser scanner. A laser 171 emits a beam 173 which is reflected off of scanning mirrors 175 and 177. Mirrors 175 and 177 are rotatable about orthogonal axes as indicated by arrows 176 and 178 so as to scan laser beam 173 in two dimensions over electrophoresis unit 181. Alternatively, the beam 173 may be scanned in only one dimension. A lens 179 brings the beam 173 parallel to optical axis 180, while a lens 183 following electrophoresis unit 181 brings the beam to a focus onto a position detector 185.

Figure 10:
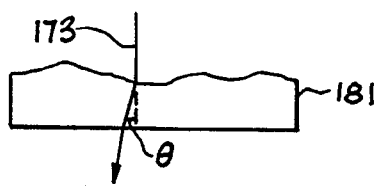
FIG. 10 is a side section of a gel electrophoresis unit demonstrating the operation of the system in FIG. 9.

Position detector 185 measures the displacement of light beam 173 due to any deviation through the electrophoresis unit 131. As seen in FIG. 10, index of refraction changes in unit 181 are optically equivalent to a surface contour, bringing about a deflection of the light beam 173 by a small angular deviation $\theta$. This slight deviation is measurable as a beam displacement at position detector 185. Integrating the measured deviation over the entire scan produces the relative wavefront modification produced by sample constituents in the electrophoresis unit 181.

The method of the present invention and system for carrying out the method uses interferometry, phase imaging and laser scanning to provide a way of imaging sample constituents without staining. This method is considerably less time consuming than the usual several hours of prior staining techniques.

I claim:

1. An electrophoretic measuring system comprising,
   a gel electrophoresis unit having gel material and sample material thereon,
   a light source emitting a collimated beam, said beam being directed toward said electrophoresis unit, said beam passing through said gel and sample material on said unit,
   shearing interferometer means disposed in the path of said light beam for producing an interferogram representing the spatial rate of change of an index of refraction of said material on said unit, said shearing interferometer means including a pair of closely spaced first and second plates in the path of said light beam, said first plate being partially reflection and partially transmissive, said second plate being in communication with means for altering the separation between said first and second plates,
   means for forming an image of said interferogram,
   means for producing a data signal from said image representing said interferogram, and
   means for processing said data signal to obtain the concentration of sample material at each position on said unit, said means for processing including means for solving
   (a) a first equation:

$$I(x) = I_0(x) + I_1(x) \cos\left(\frac{2\pi}{\lambda} \Delta_0(x)\right)$$

obtained for a first plate separation $Z_0$,
(b) a second equation:

$$I(x) = I_0(x) - I_1(x) \sin\left(\frac{2\pi}{\lambda} \Delta_0(x)\right)$$

obtained for a second plate separation $Z_0 + \lambda/4$, and
(c) a third equation:

$$I(x) = I_0(x) - I_1(x) \cos\left(\frac{2\pi}{\lambda} \Delta_0(x)\right)$$

obtained for a third plate separation $Z_0 + \lambda/2$, for $\Delta_0(x)$,
where $I(x)$ is the light intensity of said interferogram, $I_0(x)$ is the light intensity of light reflected from said first plate, $I_1(x)$ is the light intensity of the light transmitted through said first plate and reflected from said second plate, $\Delta_0(x)$ is an optical path difference for said light beam through said gel and sample material on said unit, x is the position with respect to said electrophoresis unit and $\lambda$ is the wavelength of said light beam.

2. The system of claim 1 wherein said light source is a laser.

3. The system of claim 1 wherein said means for producing a data signal is an image digitizer disposed for scanning said image, said image digitizer producing a data signal corresponding to the light intensity $I(x)$ of said interferogram for each of said first, second and third plate separations.

4. The system of claim 1 wherein said means for processing further comprises means for integrating $\Delta_0(x)$ over positions x to obtain the phase $\phi(x)$ of said beam after having passed through said gel and sample material on said unit, said phase $\phi(x)$ being proportional to the concentration of sample material at each position x on said unit.

5. A method of measuring the positions of sample material components on a gel electrophoresis plate comprising,
(a) illuminating a gel electrophoresis plate with a collimated light beam, said plate having gel material and sample material thereon, sample material on said plate being characterized by a different index of refraction than an index of refraction of gel material on said plate, the different indices of refraction creating optical path differences for said light beam passing through said gel and sample materials on said plate, said optical path differences modifying the phase of wavefronts of said light beam,
(b) passing said modified light beam through a shearing interferometer, said shearing interferometer including a pair of closely spaced plates in the path of said modified light beam, said plates having an adjustable spacing, the passing of said modified light beam through said shearing interferometer causing
(1) a splitting of said modified light beam into substantially identical first and second beams,
(2) a spatial displacing of said second beam by a small distance with respect to said first beam, and
(3) a recombining of said first beam with said displaced second beam,
said splitting, displacing and recombining being performed by said pair of closely spaced plates, said interferometer thereby producing an interferogram representing the spatial rate of change of the index of refraction of material on said plate at every point of said plate,
(c) scanning said interferogram with an image digitizer, said image digitizer producing a data signal corresponding to said interferogram, and
(d) integrating said data signal over space, said integrating of said data signal including
(1) solving a set of three equations for $\Delta_0(x)$, where a first of said equations is $$I(x) = I_0(x) + I_1(x) \cos\left(\frac{2\pi}{\lambda} \Delta_0(x)\right)$$

obtained for a first plate separation $Z_0$,
a second of said equations is $$I(x) = I_0(x) - I_1(x) \sin\left(\frac{2\pi}{\lambda} \Delta_0(x)\right)$$

obtained for a second plate separation $Z_0 + \lambda/4$, and a third of said equations is $$I(x) = I_0(x) - I_1(x) \cos\left(\frac{2\pi}{\lambda} \Delta_0(x)\right)$$

obtained
for a third plate separation $Z_0 + \lambda/2$,
where $I(x)$ is the light intensity of said interferogram, $I_0(x)$ is the light intensity of light reflected from said first plate, $I_1(x)$ is the light intensity of light transmitted through said first plate and reflected from said second plate, $\Delta_0(x)$ is an optical path difference for said light beam through said gel and sample material on said unit, x is the position with respect to said electrophoresis unit and $\lambda$ is the wavelength of said light beam, and
(2) integrating $\Delta_0(x)$ over position x, said integrated signal representing phase values of said modified wavefronts, said phase values being proportional to a concentration of sample material relative to gel material at each point on said plate.

6. The method of claim 5 wherein said gel electrophoresis plate is illuminated with a laser beam.

* * * * *